United States Patent [19]
Freeman

[11] Patent Number: 5,140,135
[45] Date of Patent: Aug. 18, 1992

[54] ADAPTIVE ICE DETECTOR CIRCUIT

[75] Inventor: Kenneth J. Freeman, Eagan, Minn.

[73] Assignee: Rosemount Inc., Eden Prairie, Minn.

[21] Appl. No.: 590,142

[22] Filed: Sep. 28, 1990

Related U.S. Application Data

[63] Continuation of Ser. No. 410,251, Sep. 21, 1989, abandoned.

[51] Int. Cl.$^5$ ............................................. H05B 1/02
[52] U.S. Cl. ................................. 219/497; 219/492; 219/494; 219/506; 340/581
[58] Field of Search ............... 219/492, 506, 494, 497, 219/499, 501, 505, 508, 203, 207; 340/581, 580

[56] References Cited

U.S. PATENT DOCUMENTS

| | | |
|---|---|---|
| 3,594,775 | 7/1971 | Fox .................................. 340/581 |
| 4,333,004 | 6/1982 | Forgue et al. ..................... 340/581 |
| 4,367,399 | 1/1983 | Anthony et al. .................. 219/492 |
| 4,640,127 | 2/1987 | Schneider ......................... 219/492 |
| 4,755,062 | 7/1988 | Meyer .............................. 340/581 |
| 4,897,527 | 1/1990 | Cripps et al. ..................... 219/492 |

Primary Examiner—Mark H. Paschall
Attorney, Agent, or Firm—Kinney & Lange

[57] ABSTRACT

An ice detector circuit controls heating of a probe detecting ice. The circuit generates an icing output as a function of a temperature output generated by the probe. A control circuit cyclically controls a start time of the heating. A time measurement circuit measures a warm-up time to a first temperature threshold below the melting temperature, and measuring a melting time to a second temperature above the melting temperature. A comparator compares the melting time to a stored comparison parameter adjusted by the warm-up time and provides the icing output.

6 Claims, 2 Drawing Sheets

ADAPTIVE ICE DETECTOR CIRCUIT

This is a continuation of application Ser. No. 07/410,251, filed Sept. 21, 1989 now abandoned.

BACKGROUND OF THE INVENTION

1. Field of the Invention

This invention relates to ice detectors for sensing icing as a function of melting of ice on a detector surface.

2. Description of the Prior Art

Icing detectors for air vehicles which heat a detection surface and measure thermal heat of fusion either during melting or refreezing of the deposited ice are known. In such ice detectors, it is difficult to accurately measure heat loss due to thermal heat of fusion because there are variable losses from other sources which add or subtract from the heat of fusion and cause errors in measurement. These other losses include convective heat loss due to varying airspeed, air temperature, and air density as well as heat loss to structures supporting the ice detector. There is thus a need to provide a more accurate measure of heat of fusion as an indication of icing.

SUMMARY OF THE INVENTION

In the present invention, an ice detector circuit adapts the operation of an ice detector probe or sensor to correct for variable heat losses associated with forced convection heat loss to the air flow over the sensor and conductive heat leakage to structures surrounding the sensor.

The ice detector circuit controls heating of a probe or detector for detecting ice having a melting temperature. The ice detector circuit generates an icing output indicating icing as a function of a temperature output generated by the probe. Control means in the ice detector circuit couple to the detector for cyclically controlling a start time of the heating. The ice detector circuit further comprises measurement means coupled to the temperature output for measuring a warm-up time to a first temperature threshold below the melting temperature, and for measuring a melting time to a second temperature above the melting temperature. Comparing means in the ice detector circuit compare the melting time to a stored comparison parameter and providing the icing output. Adjusting means adjust the start time as a function of the warm-up time such that the start time is adjusted for non-icing heat loss from the detector.

In a preferred embodiment, the adjusting means further adjusts the cycling rate as a function of the melting time, and adjusts the stored comparison parameter as a function of the warm-up time.

DETAIL DESCRIPTION OF THE PREFERRED EMBODIMENTS

Figure 1:
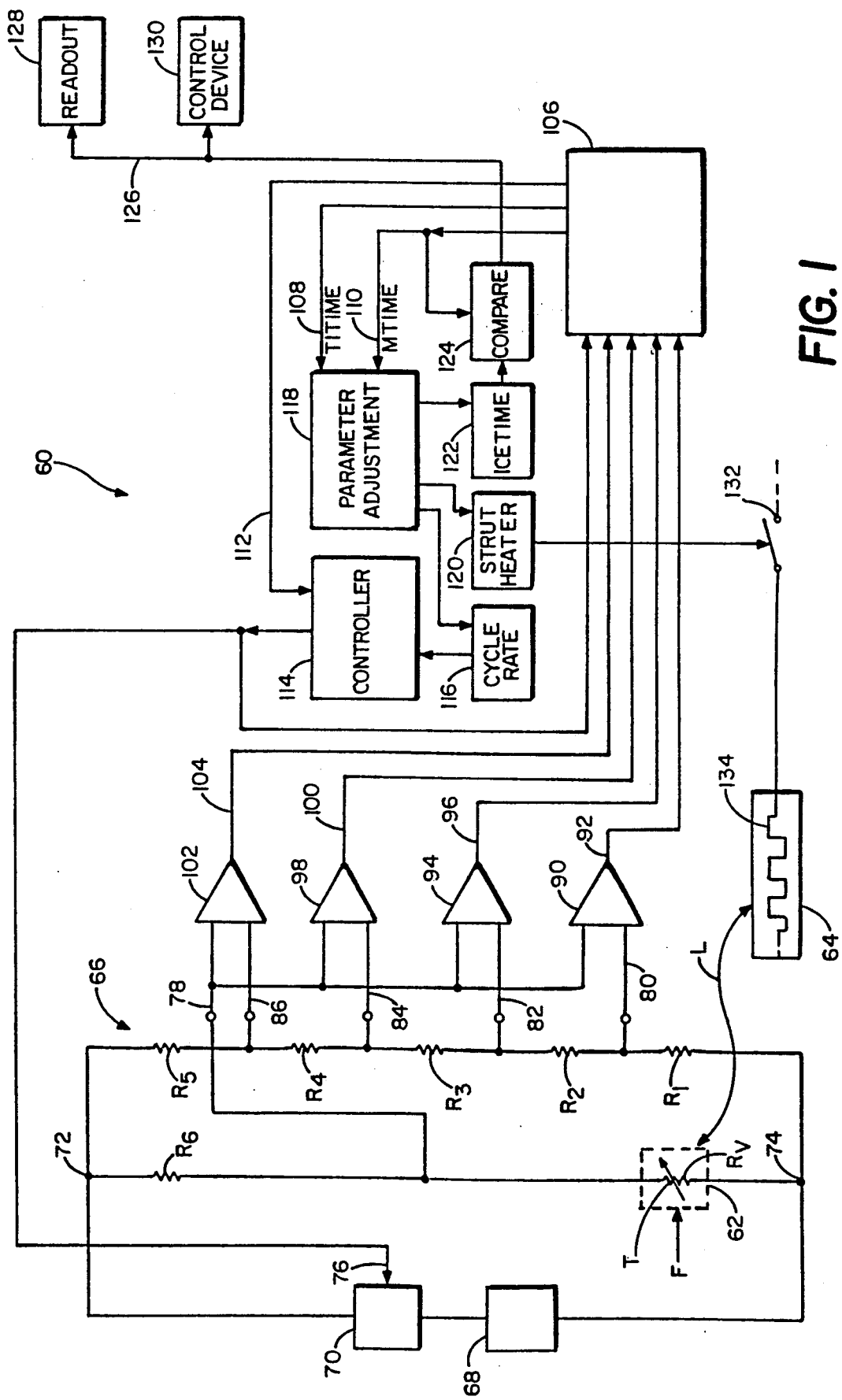
FIG. 1 shows a schematic diagram of the preferred embodiment of the invention.

FIG. 1 shows a partial block, partial schematic diagram of a preferred embodiment of an ice detector circuit 60 coupled to ice detector probe 62 having a self-heating resistance temperature sensor $R_v$ which is disposed to receive a flow, arrow F, of air subject to icing. Temperature sensor $R_v$ can comprise a self-heating, thin film platinum resistance thermometer. Ice detector 62 is mounted to a strut 64 on an aircraft, and there is some undesired thermal leakage L between the probe 62 and the strut.

Ice detector circuit 60 includes resistors $R_1$, $R_2$, $R_3$, $R_4$, $R_5$ and $R_6$ which are connected to resistance $R_v$ to form a resistance bridge circuit 66 as shown in FIG. 1. Excitation source 68 is coupled via solid state switch 70 to excitation terminals 72, 74 of bridge 66. When switch 70 is closed by application of a control output to line 76, the excitation source 68 energizes the bridge 66. When the bridge 66 is energized, the resistance $R_v$ heats the probe 62 for sensing icing. Resistance $R_v$ in probe 62, which is part of bridge 66, provides a temperature output on line 78 which is representative of temperature T of probe 62. Resistors $R_1$, $R_2$, $R_3$, $R_4$, $R_5$ are connected in series between the excitation terminals 72, 74 to form a resistive potential divider. The resistive potential divider has multiple taps 80, 82, 84, 86 generating potentials representing successively higher temperatures thresholds in comparison to the temperature output on line 78.

A comparator 90 compares the temperature output on line 78 to the potential at tap 80 and provides an output on line 92 indicating that temperature T has reached a first threshold temperature below the melting point of ice. A comparator 94 compares the temperature output on line 78 to the potential at tap 82 and provides an output on line 96 indicating that temperature T has reached a second threshold, which is above the melting point of ice. A comparator 98 compares the temperature output on line 78 to the potential at tap 84 and provides an output on line 100 indicating that temperature T has reached a point at which substantially all ice is removed from probe 62. A comparator 102 compares the temperature output on line 78 to the potential at tap 86 and provides an output on line 104 indicating that temperature T is outside of a normal temperature range and that there is therefore a malfunction.

The comparator outputs on lines 92, 96, 100, 104 which indicate that successively higher temperature thresholds have been reached by the temperature T are coupled to a measurement circuit 106. The control output on line 76 is also coupled to measurement circuit 106, providing an indication of the start of heating. Measurement circuit 106 measures the warm-up time between the start of heating and the time at which temperature T reaches the first threshold and provides an output T1TIME on line 108 indicating the warm-up time. The measurement circuit further measures the melting time between the first and second thresholds and provides an output MTIME on line 110 indicative of melting time.

Measurement circuit 106 also measures the time at which temperature T reaches the third threshold and provides an end-of-heating output on line 112 indicating when the third threshold has been reached. A controller 114 controls the control output on line 76 as a function of the end-of-heating output on line 112 and a stored adjustable parameter CYCLE RATE shown in a storage element or memory at 116. During operation, controller 114 starts a heating period by providing the control output on line 76 to enable switch 70 to connect excitation source 68 to bridge 66. Connection of the bridge circuit to the excitation source 68 causes resistor $R_v$ to begin heating the probe 62. When temperature output T exceeds the thresholds set by the voltage divider, the comparator outputs 92, 96, 100 successively change state indicating that temperature T has reached successively higher threshold temperatures. When the temperature T reaches the third threshold, controller 114 opens switch 70 and the sensor is allowed to cool to the end of the cycle. The length of the cycle is controlled by CYCLE RATE.

Parameter adjustment circuit 118 receives outputs T1TIME and MTIME on lines 108 and 110 and adjusts parameters CYCLE RATE, STRUT HEATER shown stored at 120 and ICETIME shown stored at 122 as explained in detail below in connection with FIG. 2.

Comparator circuit 124 compares the stored comparison parameter ICETIME to the sensed melting time variable MTIME and provides icing output on line 126 indicating icing. The icing output on line 126 can be coupled to a readout 128 or control device 130 controlling de-icing of aircraft surfaces.

The parameter STRUT HEATER stored at 120 controls the actuation of solid state switch 132 controlling energization of a heater 134 in strut or mounting structure 64 for probe 62.

Figure 2:
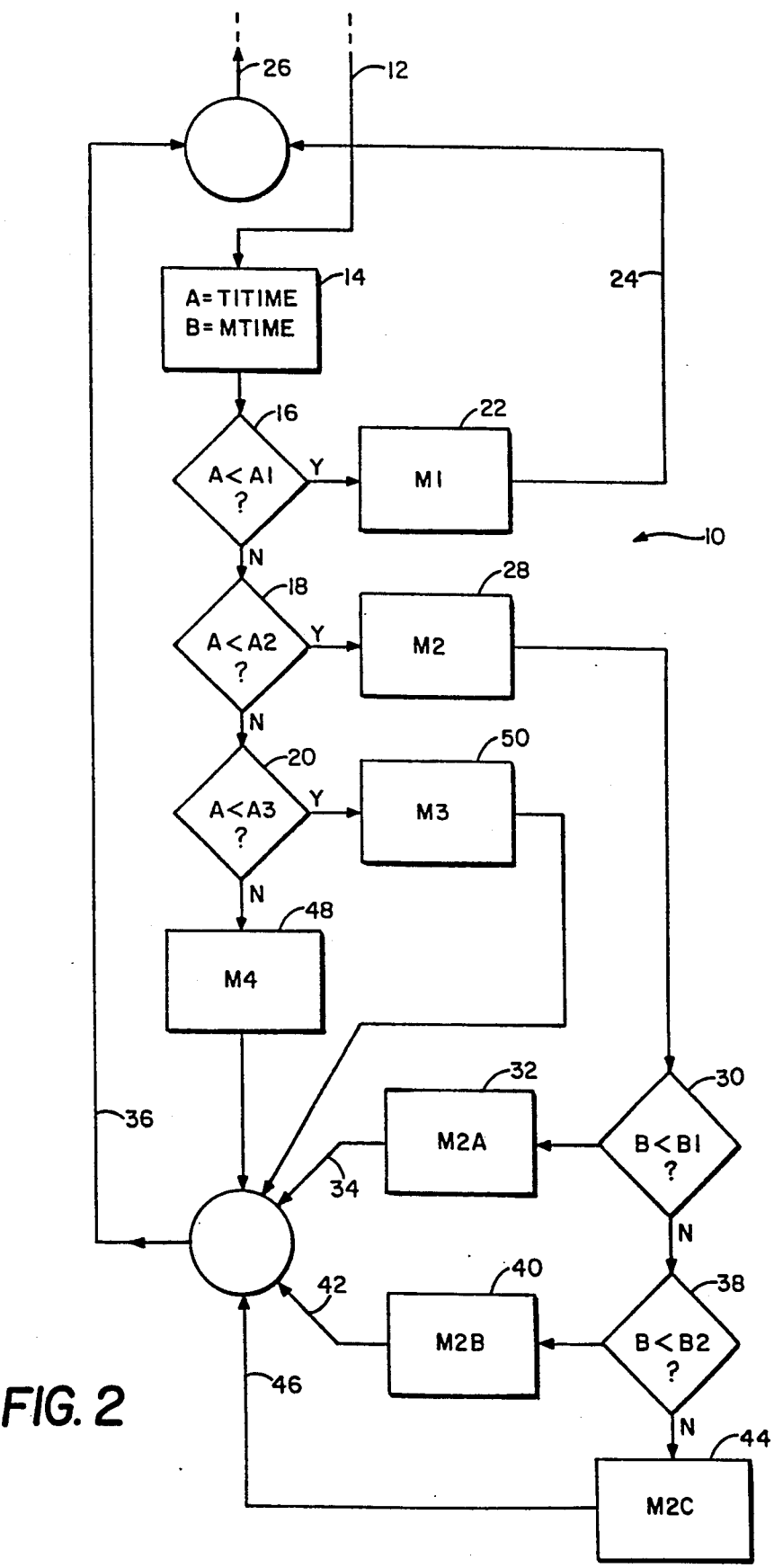
FIG. 2 shows a flow chart of the parameter adjustment circuit.

FIG. 2 shows a flow chart or algorithm performed by parameter adjustment circuit 118. Parameter adjustment circuit 118 can comprise digital logic or a microprocessor system, and the microprocessor system can be common to other functions performed in the ice detector circuit 60, as well. The algorithm shown in FIG. 2 is an adaptive control algorithm which adapts parameters used in controlling the ice detector and the icing output to ambient conditions of heat loss and icing. The algorithm is executed once for each heating cycle of probe 62. Parameter adjustment circuit 118 starts execution of the algorithm at line 12 in FIG. 2, and updates measured times A and B with current values of T1TIME and MTIME respectively as shown in block 14. T1TIME is the time interval between starting heater energization and sensing the first temperature threshold. MTIME is the ice melting time interval between sensing the first and second detection thresholds.

Time A, the time to heat the sensor to the first temperature threshold correlates with forced convection heat loss to the air flow F and conductive heat leakage L to structures (heat sinks) 64 surrounding the sensor. When the ambient temperature is lower, it takes longer to heat the sensor 62 to the first temperature threshold since the surrounding heat sinks are at a lower temperature. Time A is therefore larger when ambient temperatures are low. When there is a larger mass flow F past the sensor 62, forced convective heat loss is larger, and time A therefore increases.

The conductive and forced convective heat losses are present during the melting time interval, and introduce error into the measurement of heat of fusion of ice on the probe. Time A represents this background heat loss which is independent of heat loss due to melting ice.

In decision blocks 16, 18, 20, the parameter adjustment circuit compares time A to stored time constants A1, A2, A3 in order to select different operation modes M1, M2, M3, M4 based on the rate of background heat loss. The operation of the ice detector is thus corrected for background heat loss.

In decision block 16, the parameter adjustment circuit compares time A to time constant A1 which, in a preferred embodiment is A1=200 microseconds. If time A is less than A1, this indicates that the ambient temperature is so warm that icing will occur only very slowly, if at all, and the parameter adjustment circuit selects mode M1 in block 22. In mode M1, the parameter adjustment circuit sets the CYCLE TIME long to allow a long time for ice to accumulate on the sensor. In a preferred embodiment, the parameter adjustment circuit 118 sets CYCLE TIME to 8 seconds in mode M1. In mode M1, parameter adjustment circuit 118 adjusts stored comparison parameter ICETIME to be long to reduce the likelihood of a false indication of icing due to noise. In a preferred embodiment, ICETIME=4 seconds in mode M1. In mode M1, parameter adjustment circuit sets parameter STRUT HEATER to a low level which shuts off the strut heater. After the parameter adjustment circuit adjusts parameters CYCLE TIME, ICETIME, and STRUT HEATER in block 22, the parameter adjustment circuit leaves the algorithm via lines 24, 26.

After completion of the algorithm, the CYCLE TIME, ICETIME and STRUT HEATER words selected by parameter adjustment circuit are available for use during the next heating cycle of the probe.

If time A is greater than constant A1, parameter adjustment circuit 118 next compares time A to a second constant A2 (larger than constant A1) in decision block 18. In a preferred embodiment A2=5 milliseconds. If time A is less than constant A2, this indicates that the ambient temperature and airflow are in a range where icing is possible, and parameter adjustment circuit selects mode M2 in Block 28. In mode M2, the constant ICETIME is set to a shorter time interval than it is in mode M1, and in a preferred embodiment, ICETIME=42 milliseconds in mode M2.

After mode M2 is selected, the parameter adjustment circuit executes decision block 30 which compares the current ice melting time B to a constant B1 which, in a preferred embodiment is B1=42 milliseconds. If time B is less than constant B1, then significant icing is not occurring and mode M2A is selected at block 32. In mode M2A, CYCLE TIME is set to 8 seconds and STRUT HEATER is set low and the strut heater is not energized. After completion of block 32, the parameter adjustment circuit leaves the algorithm via lines 34, 36, 26.

If icing time B is not less than threshold B1, the parameter adjustment circuit advances to execute decision block 38. In decision block 38, icing time B is compared to a constant B2, and in a preferred embodiment B2=220 milliseconds. If icing time B is less than constant B2, then moderate icing is occurring and mode M2B is selected. In mode M2B, STRUT HEATER is set low, and the CYCLE TIME is set to a shorter time interval than it is in mode M2A in block 40. In a preferred embodiment, CYCLE TIME is set in mode M2B to 4 seconds. After execution of the instructions in block 40, the parameter adjustment circuit leaves the algorithm via paths 42, 36 and 26.

If icing time B is not less than threshold B2, then there is heavy icing and the parameter adjustment circuit advances from decision block 38 to block 44. In block 44, the parameter adjustment circuit sets the STRUT HEATER to a high level and the strut heater is turned on. In mode M2C, the parameter adjustment circuit also sets the CYCLE TIME to a short interval, in a preferred embodiment CYCLE TIME=2 to 3 seconds, to prevent ice from accumulating too thickly on the sensor. After completion of block 44, the parameter adjustment circuit leave the algorithm via paths 46, 36, 26.

Looking back now at decision block 18 discussed above, if the time A is not less than constant A2, parameter adjustment circuit advances to decision block 20. In decision block 20, parameter adjustment circuit compares time A to constant A3. Constant A3 is preferably 50 milliseconds. If time A is less than 50 milliseconds, then there is moderate heat loss from the sensor and the parameter adjustment circuit selects mode M3 at 50. In mode M3, ICETIME is adjusted to a longer time than in mode M2 and parameter STRUT HEATER is set high. In a preferred embodiment, ICETIME=45 milliseconds in mode M3. If time A is longer than 50 milliseconds, then the parameter adjustment circuit selects mode M4 at 48, indicating a high rate of background heat loss from the sensor, such as is encountered at low ambient temperatures. In mode M4, ICETIME is set higher than in Mode 3, and in a preferred embodiment, ICETIME=55 milliseconds in mode 4 and STRUT HEATER is set high. After completion of block 48 or 50, the parameter adjustment circuit 118 exits the algorithm via paths 36, 26.

The strut heater is energized when ice is detected and the ambient temperature is below the setpoint. This reduces power consumption by the strut heater, extends the life of the heater and electrical parts in the strut, and increases sensitivity of the sensor to icing at near freezing temperatures by reducing heat conduction from the strut to the sensor surface. The rapid response of the strut heater to icing events keeps ice from building up on the strut.

While the invention has been described with reference to preferred embodiments, workers skilled in the art will recognize that changes may be made in form and detail without departing from the spirit and scope of the invention.

What is claimed is:

1. A circuit for controlling heating of a probe detecting ice having a melting temperature and for generating an icing output indicating icing as a function of a temperature output generated by the probe, comprising:

control means coupled to the probe for controlling the duration of cyclical periods of heating and cooling of the probe;

measurement means coupled to the temperature output for measuring a warm-up time of the probe from onset of heating to a first temperature threshold below the ice melting temperature, and for measuring an ice melting time to a second temperature threshold above the ice melting temperature;

comparing means for comparing the ice melting time to a stored comparison parameter and providing the icing output; and adjusting means for adjusting the duration of the cooling period for subsequent cyclical periods of heating and cooling of the probe as a function of the warm-up time to compensate for non-icing heat loss from the probe.

2. The circuit of claim 1 wherein the adjusting means further adjusts the duration of the heating period as a function of the ice melting time.

3. The circuit of claim 1 wherein the adjusting means further adjusts the stored comparison parameter as a function of the warm-up time.

4. The circuit of claim 3 wherein the adjusting means further adjusts the stored comparison parameter as a function of the ice melting time.

5. The circuit of claim 1 wherein the detector is mounted to a heatable mount and the adjusting means further adjusts the heating of the mount as a function of the warm-up time.

6. The circuit of claim 5 wherein the adjusting means further adjusts the heating of the mount as a function of the ice melting time.

* * * * *

UNITED STATES PATENT AND TRADEMARK OFFICE
CERTIFICATE OF CORRECTION

PATENT NO. : 5,140,135
DATED : August 18, 1992
INVENTOR(S) : KENNETH J. FREEMAN

It is certified that error appears in the above-identified patent and that said Letters Patent is hereby corrected as shown below:

On the title page, item [56], under U.S. PATENT DOCUMENTS, insert the following:

```
4,036,457  7/1977  Volknea et al. .......219/209
4,522,512  6/1985  Atkins................219/505
4,570,881  2/1986  Lustenberger..........244/134F
4,687,163  8/1987  Ringer................219/486
```

FOREIGN PATENT DOCUMENTS

WO 88/09980    12/1988

Signed and Sealed this

Fifth Day of October, 1993

Attest:

BRUCE LEHMAN

Attesting Officer

Commissioner of Patents and Trademarks